United States Patent [19]

Harrigan et al.

[11] Patent Number: 4,853,996
[45] Date of Patent: Aug. 8, 1989

[54] PATIENT BED RESTRAINT

[76] Inventors: Linda M. Harrigan, 201 Eric Ct., Rohnert Park, Calif. 94928; Marlene H. Jaworski, 906 Smith, Alturas, Calif. 96101

[21] Appl. No.: 252,145
[22] Filed: Oct. 3, 1988

Related U.S. Application Data

[63] Continuation-in-part of Ser. No. 178,635, Apr. 7, 1988, abandoned.

[51] Int. Cl.[4] ............................................. A61F 13/00
[52] U.S. Cl. ......................................... 5/494; 128/873
[58] Field of Search ............... 5/424, 494, 496, 498, 5/499; 2/114; 128/869, 871, 875

[56] References Cited

U.S. PATENT DOCUMENTS

| | | | |
|---|---|---|---|
| 1,079,798 | 11/1913 | Painter . | |
| 1,403,873 | 1/1922 | Scott | 5/494 |
| 1,802,540 | 4/1931 | Schmidt | 5/494 X |
| 2,140,797 | 12/1938 | Hammerman . | |
| 2,313,337 | 3/1943 | Gurke | 5/496 X |
| 2,325,097 | 7/1943 | Behringer | 5/494 X |
| 2,328,938 | 9/1943 | Wilson . | |
| 2,374,712 | 5/1945 | Steigerwald . | |
| 2,439,101 | 4/1948 | Rogers . | |
| 3,858,256 | 1/1975 | Beer | 5/496 |
| 3,872,524 | 3/1975 | Hummel | 5/494 X |
| 3,906,559 | 9/1975 | Bahr | 5/496 |
| 4,653,131 | 3/1987 | Diehl . | |
| 4,679,267 | 7/1987 | Thiele . | |

FOREIGN PATENT DOCUMENTS 1201731  8/1970  United Kingdom .................... 5/498

Primary Examiner—Michael F. Trettel

[57] ABSTRACT

This invention provides a safe and comfortable bed restraint device for people who are mentally and or physically impaired and who could harm themselves or others if not restrained. The device is structured as a mattress covering with an upper torso fitting garment and a separate leg fitting panel both attached to the mattress covering structure. The assemblage is secured to the foot of a bed frame by two reinforced straps. The wearer is comfortably retained in a supine or side position while still having normal range of movement of the arms and legs.

2 Claims, 2 Drawing Sheets

PATIENT BED RESTRAINT

BACKGROUND OF THE INVENTION

This is a continuation in part of application Ser. No. 07/178,635 filed 04/07/88, now abandoned.

1. Field of the Invention:

This invention relates to patient restraint devices for bed use designed for mentally or physically impaired people to prevent falls and injury.

2. Description of the Prior Art:

Some hospitals and all convalescent hospitals and nursing homes have experienced the need to retain certain patients in bed, due to their mental confusion. This is to prevent injury to the patient and others. Several major problems have been found with the use of the presently available bed restraint devices. One of the problems is the danger of the restraint restricting the patient to the point of cutting off circulation or even strangulation. Another problem arises concerning the occurrence of skin breakdown and irritation when elderly patients lay on zippers, buttons or bulky folded portions of material. This problem is compounded when the patient is forced to sleep on his back without the ability to rool onto his side. The frail condition of their skin, due to poor circulation and age, makes them prone to minor irritations and decubitus. A third problem concerns the fact that, although elderly patients are frail, they are also sometimes very agile and persistent when it comes to "undoing" restraints. A major problem found in the past art restraints is their inconvenience for nurses to apply and remove the restraints from the often heavy adult patients. Urinary catheters are used with many patients who require bed restraints. Since it is necessary to inspect and clean a catheter once a day, a bed restraint that allows such inspection without complete removal of the restraint is an advantage.

Most of the past art patents examined in a patent search are specifically directed towards use with infants or small children and not adult patients. However, if adaptations were made in size to accommodate adults, there would still exist several problems in the design and structure of those devices which would make them unsuitable. Several of the past art devices examined, specifically those taught in U.S. Pat. Nos. 2,140,797, 2,374,712, 4,653,131 and 4,679,267, are designed with zippers, bulky folds or attachment means located on the back of the garment where they could prove to cause skin irritation. The devices taught in U.S. Pat. No. 2,140,797, 1,079,798, 2,374,712, and 4,679,267 have zippers or attachment ties located within reach of the wearer, where they can be opened or untied by the patient. Past art devices of U.S. Pat. Nos. 1,403,873 and 2,439,101, show no securing means of the device to the bed, which although may be suitable for infants, would not prove to retain an adult who could merely pull the sides out from between the mattress and box springs. Several of the restraint garments, such as those found in U.S. Pat. Nos. 1,403,873, 2,140,797, 1,079,798, and 2,328,038, are structured in a two fold design, having the person lie between the top and bottom section. This design of bed restraint would not be suitable for those elderly patients who unfortunately have become incontinent and require special protective bed linens. One device taught in U.S. Pat. No. 4,653,131, could prove to be potentially dangerous if the patient slipped down in bed being restrained by the device only by the neck. Another problem found in many past art devices such as taught in U.S. Pat. No. 1,079,798, 2,328,038, 2,439,101, and 4,653,131, would be the use of these garment devices with patients having indwelling urinary catheters. Some disoriented and confused patients actually pull our their catheters, sometimes causing injury to themselves and always necessitating a new, sterile unit to be reinserted. These past art devices leave gaps or openings on the sides where the patient could slide his or her hand and gain access to the catheter.

Some past art devices, such as the one taught in U.S. Pat. No. 2,374,712 for example, are specifically for small children. Such devices are structured in a manner which necessitates the lifting of the child onto or out of the restraint. This type of structuring is fine for small light weight children, but is completely unsuitable for adult patients. With this type of device, nurses would have to reach over to the center of the bed and lift the patient. Due to the positioning of both the patient and the bed, it would be impossible for the nurses to bend their knees to lift the weight in a proper lifting fashion. Consequently back injuries would occur. Also, at least two nurses would be need for such a task.

Our restraint garment overcomes the previously mentioned disadvantages and provides new and useful benefits to the field of bed restraint devices for adult patients as will be shown in the following summary and specification.

SUMMARY OF THE INVENTION

In practicing our invention we have developed a bed restraint device for use with mentally and physically impaired people. Our invention comprises a wide fabric mattress covering top panel having a top or head end structure similar to a fitted sheet for slip on attachment under the head of a bed mattress. The side panels of the restraint are attached to bottom panel sections design to be tucked horizontally under the mattress. At the foot end of the bottom panel sections are securing tie straps for removably attaching the foot end of the restraint to the bed frame. Positioned centrally toward the head end of the restraint is an opening sized for the patient's upper body to pass through. Sewn over the central opening is a fabric shirt-like garment having a neck opening and two arm apertures with sleeves designed to cover the upper torso of the patient. Transversing the lower edge of the garment opening on the underneath side of the top panel is a wide retaining strap. The retaining strap is designed to be positioned snugly across the back below the shoulders of the patient. The tightness of the retaining strap is somewhat critical, and usually requires sewing in the hospital to adjust the strap to the proper size for each wearer. In use, the patient is positioned between the retaining strap and the top panel. The retaining strap helps to prevent the patient from pulling his arms out of the sleeves, and the garment off over his head. It also helps to prevent him from sliding downward.

Sewn centrally to the underside of the top panel between the foot end of the restraint and the garment opening, is a substantially rectangular fabric flap or panel having two side by side horizontally positioned leg apertures. The top edge of the flap is sewn to the top panel, leaving three edges of the four edged panel free. This leg panel fits over the legs of the patient to prohibit him from sliding downward underneath the top panel. The placement of the leg panel is somewhat critical relative to the garment, and is also often attached to the top panel at the hospital in order to ensure a proper fit on the wearer. If the leg panel is positioned too close to the garment, it becomes difficult or impossible to put on and remove the restraint from the patient. If the leg panel is positioned too far from the garment in the top panel, then the patient might be able to slip downward out of the shirt-like garment and become trapped underneath the top panel. Also, since the leg panel does not extend completely between the crotch of the patient, it does not interfere with catheters or the inspection thereof.

To put the restraint onto a patient, the patient is sat or laid on the bed. With the restraint free of the bed, the patient's legs are inserted through the leg openings of the leg panel which is then pulled up to the crotch area of the wearer. The patient's upper body and head is then positioned somewhat toward his knees where the retaining strap and garment is pulled over the front of the body positioning his head through the neck opening and his arms through the arm apertures. The retaining strap is positioned across the back just below the shoulders. The patient is then laid on his back in the center of the bed. The head of the top panel is secured to the head of the mattress by slipping it over and under the end of the mattress. The sides of the restraint are positioned on the sides of the mattress, and bottom panel sections attached to the side panels are then tucked underneath the mattress. The tie straps attached to each inner corner at the foot end of each of the bottom panel sections are then tied to the bed legs or other framing member at the foot of the bed out of reach of the patient.

The patient is now securely restrained in the bed with most of his body under the top panel of the restraint, and his upper torso in the shirt-like garment. The patient's head and arms are free to move above the top panel, and his legs are free to move below the top panel. Loose fabric on each side of the wearer in the top panel allows the patient to roll onto his side if desired, but the fabric is not so loose to allow him to slip off the side of the bed. The patient is prevented from escaping upward through the garment by the neck opening and the retaining strap. He is prevented from sliding downward out of the shirt-like garment by the leg panel and the retaining strap. Because of the position of the tie straps at the foot of the bed, he is prevented from untying the restraint.

To remove the restraint, the nurse first unties the straps at the foot of the bed whereby gaining enough slack to be able to slip the head end and bottom panel sections of the restraint out from underneath the mattress. The nurse then raises the patient's upper torso bending him toward his knees. If the patient is too heavy and incapable of assisting in this action, the nurse can raise the head of the bed electrically or manually since most hospital beds are structured for this purpose. Bending the patient forward shortens the length of the patient's body between the leg panel and the shirt-like garment thus allowing the garment to be pulled over and off the patient's head and arms. Once the patient's upper torso is free, and since the leg panel doesn't fit underneath the wearer's buttocks, the panel can be easily slipped off the legs.

With our restraint structured as it is, the patient is securely and comfortably held. The wide width of the top panel allows the patient the option of sleeping on his side to increase comfort and reduce bed sores. Also, since no heavy lifting is required, our invention allows one nurse to both apply and remove the restraint from the patient in most cases. Because the leg panel is a flap, a nurse wishing to change a wearer's catheter need only untie the tie straps and fold back the foot end of the restraint to access the catheter.

Therefore it is a primary object of our invention to provide a bed restraint device which is extremely difficult if not impossible for the user to remove, having the securing means out of reach and therefore impossible for the wearer to untie.

Another object of our invention is to provide a bed restraint device which is comfortable and non-restrictive allowing for free movement of all extremities as well as side to side repositioning of the patient.

A further object of our invention is to provide a bed restraint which inhibits the wearer from removing catheters, colostomy bags or dressings on the lower part of the body while leaving the hands and arms unbound.

An even further object of our invention is to provide a bed restraint which prohibits the patient from sliding downward becoming trapped with his head under the restraint.

A still further object of the invention is to provide a restraint which meets the above objects which is simple and easy for a nurse to use on a patient.

Further objects and advantages of our device will prove evident with a reading of the specification and subsequent comparison of the numbered parts with those shown in the accompanying drawings.

DESCRIPTION OF THE PREFERRED EMBODIMENT

Figure 1:
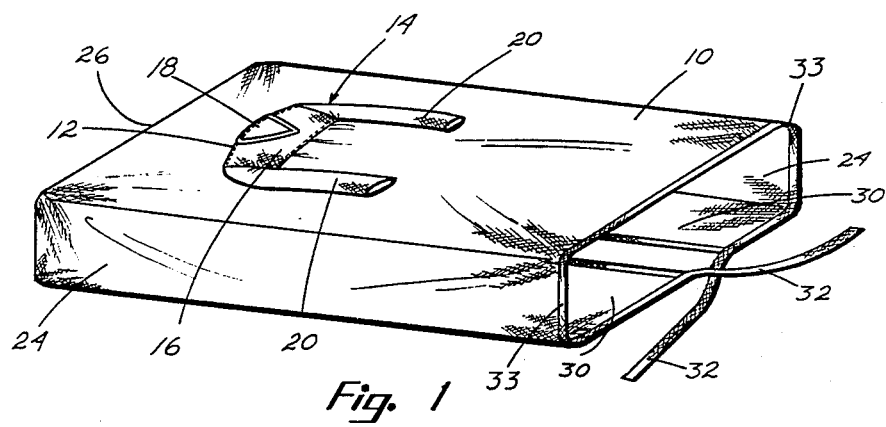
FIG. 1 illustrates the preferred embodiment in a top perspective view.
Figures 2, 3:
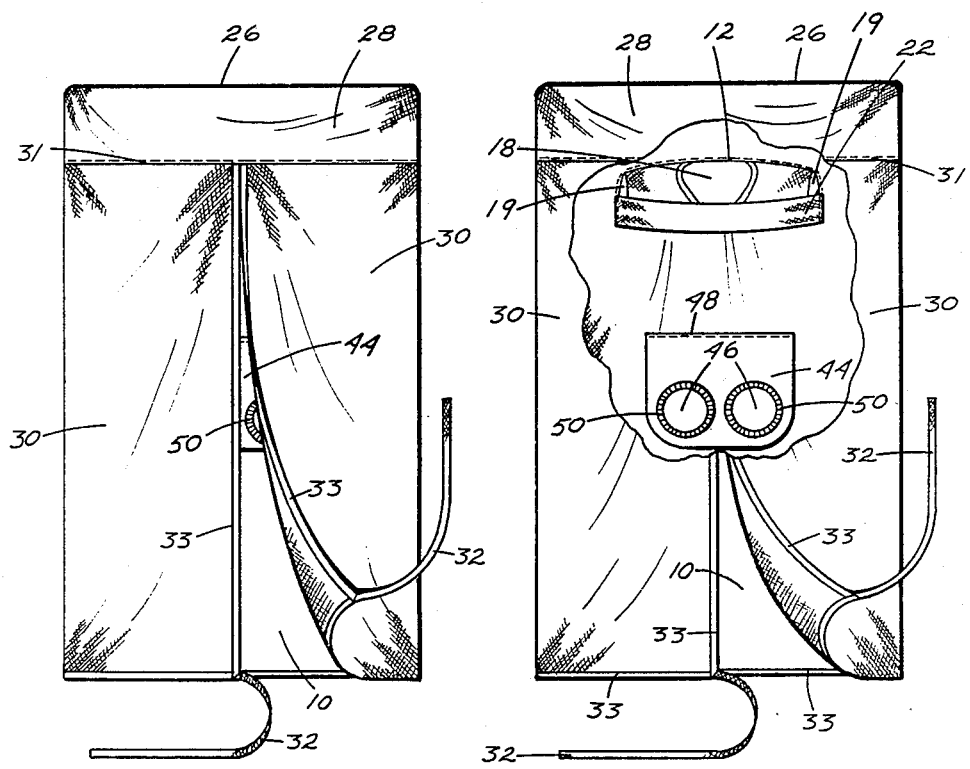
FIG. 2 is a rear view of the preferred embodiment showing the bottom side of the bottom panel sections with tie straps on each inner corner.
FIG. 3 is a rear view of the preferred embodiment with a cutaway section showing the underside of the top panel having the garment opening, retaining strap, and leg panel.

Referring now to the drawings and to FIG. 1 where the preferred embodiment is illustrated. The following description and relative positioning of the parts of the restraint are described as they would be in use on a bed mattress. The restraint device is comprised of a rectangular central opening 12 located adjacent the head or top end, oriented for placement towards the head of a bed. Central opening 12 is edgewardly affixed with retaining garment 14, shown in FIG. 1 and 4, which is comprised of front section 16, having a head-sized neck opening 18, and two armsized arm apertures 19 with sleeves 20 on either side. Retaining garment 14 made of fabric, is sewn over central opening 12 with neck opening 18 adjacent the top end and the sleeves 20 adjacent the opposite bottom end. Fabric retaining strap 22, shown in FIG. 3, is affixed at each end to the connecting junction of central opening 12 and each sleeve 20.

Affixed on one edge centrally by way of leg panel seam 48 to the underside of top panel 10, and more toward the bottom or foot end of the restraint than retaining garment 14, is fabric leg panel 44. Leg panel 44 has four outer edges and is affixed upwardly at leg panel seam 48 only, leaving three free edges. Leg panel 44 is structured with two leg openings 46 positioned horizontally side by side toward the lower distal end of leg panel 44. Leg openings 46 are rimmed with a stretchy rib knit material 50 for comfort.

Figure 4:
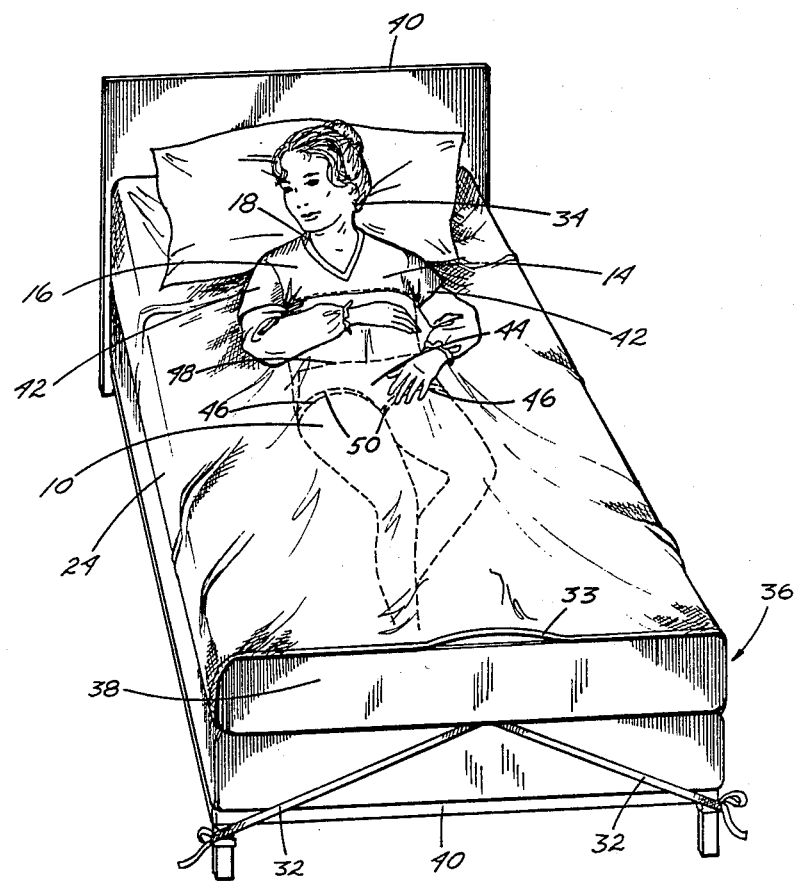
FIG. 4 is an illustration of the preferred embodiment in use. The leg panel and patient's legs under the top panel are shown with dotted lines.

Permanently attached to each lengthwise side of top panel 10 is one downwardly vertically positioned side panel 24, shown in FIG. 1 and 4, extending the full length thereof, Vertical front end panel 26 is attached edgewardly to top panel 10 at the head end of the restraint, extending downwardly to attach on each vertical end with the adjacent vertical end of each side panel 24. The lower side of the preferred embodiment at the top or head end is comprised of small rectangular horizontal end panel 28 permanently attached at right angles to the lower edge of vertical front end panel 26 and a short section of the lower edge of each side panel 24, shown best in FIG. 2. Horizontal end panel 28 is attached to the top end edges of two rectangular horizontal bottom panel sections 30 by elasticized seam 31. The outer lengthwise edges of bottom panel sections 30 are attached to the lower edges of side panels 24, also shown in FIG. 2. Assembled horizontal end panel 28 and both bottom panel sections 30 are equal in size to the unstretched to top panel 10. Top panel 10 being unstretched, having loose fabric on each side of garment 14 and leg panel 44 allows a wearer 34 the option of sleeping on his side. The inner, interfacing lengthwise edges of each horizontal bottom panel section 30, centrally under mattress 38, are unattached to the rest of the restraint device and each other. The two interfacing corners of horizontal bottom panel sections 30 at the foot end of the restraint are permanently affixed with reinforced edging 33 which extends past the edge of each bottom panel section 30 a specific distance to form reinforced tie straps 32, as seen in FIG. 1 and 2. Reinforced edging 33 extends around the edges of the opened bottom end of the preferred embodiment providing added strength against daily wear and tear, as seen in FIG. 1. The assembled restraint is sized sufficiently to be fitted over conventional bed mattress 38, leaving ample loose fabric on each side of retaining garment 14 and leg panel 44 for wearer 34 to sleep on his back or either side.

To put the restraint onto wearer 34, wearer 34 is sat or laid on bed 36. With the restraint free of bed 36, the legs of wearer 34 are inserted through leg openings 46 leg panel 44. The wearer's 34 upper torso and head is then positioned somewhat toward his knees where retaining strap 22 and retaining garment 14 is pulled over the wearer's 34 front, positioning his head through neck opening 18 and his arms in sleeves 20. Retaining strap 22 is positioned across the wearer's 34 back just below the shoulders. Wearer 34 is then laid on his back in the center of bed 36 with his head toward the head of mattress 38. Vertical front end panel 26 is pulled down over the vertical end of the head of mattress 38, and horizontal end panel 28 positioned underneath mattress 38. Both bottom panel sections 30 are tucked horizontally under mattress 38 and the bottom section of top panel 10 is brought down to the foot of bed 36. Reinforced tie straps 32 are pulled tight at the foot of bed 36 and the left strap 32 is tied to the right side of bed frame 40, and the right strap 32 is tied to the left side of bed frame 40, as seen in FIG. 4. The fitted restraint device can be used as a top sheet or normal bed clothing can be applied over the restraint.

Wearer 34 is now prevented from getting up out of bed 36 or even sitting up due to the top end of the restraint being retained over mattress 38. Since wearer 34 cannot sit up in bed 36 he cannot lean down and untie reinforced tie straps 32 at the foot of bed frame 40 nor can she pull the top or side sections loose and slide out due to the cross over tieing method of reinforced straps 32. Sliding down between top panel 10 and bed 36 is restricted by leg panel 44, which must be positioned accurately from retaining garment 14 for wearer 34. Retaining strap 22 helps prevent wearer 34 from pulling retaining garment 14 over his head and also helps prevent him from sliding downward.

The restraint is provided in four sizes including small, medium, large, and extra large, and would effectively accommodate most wearers 34. However, as stated, there would arise situations where the four provided sizes would not be dimensioned correctly for certain wearers 34 and simple sewing alterations can be used correct the problem. One end of retaining strap 22 can be detached by removing the seam and resown after either lengthening or shortening it the desired distance. The preferred suggested alteration method would be to acquire a restraint device that is slightly larger than desired and shorten retaining strap 22 and remove the excess length by cutting. This would prevent the excess material from bunching and causing a pressure area.

The restraint device, except for retaining garment 14 and leg panel 44, is manufactured of a tough, durable, smooth fabric which is designed to withstand repeated laundering and excessive wear and tear. Retaining garment 14 is manufactured of a soft pliable fabric which is comfortable and will not chaff or irritate the skin, yet is also sufficiently non-elastic to help prevent wearer 34 from stretching the material and removing the device. Leg panel 44 is also manufactured of a tough pliable non-elastic fabric with leg openings 46 rimmed with elastic rib knit material 50 for comfort and fit.

A second embodiment of the restraint device is provided wherein short sleeves 42 are used in retaining garment 14.

Although we have described embodiment of our patient bed restraint with considerably details in the foregoing specification, it is to be understood that modifications in the design and structure may be practiced which do not exceed the intended scope of the appended claims.

We claim:
1. A bed restraint device for human use comprising;
a fabric mattress covering, horizontally oriented lengthwise having a head end and foot end correspondingly positioned with a rectangular mattress having a head end a foot end and sides extending between; there being a flat substantially rectangular top panel having a rectangular opening adjacent said head end thereof affixed with a soft pliable material structured as a upper torso fitting garment having a head-sized aperture between two arm-sized apertures; a wide strap fitted crosswise in said rectangular opening beneath said garment with said strap sized to be positioned behind the shoulders of a human with said human in said garment; a substantially rectangular fabric leg panel affixed centrally to the underside of said top panel between said garment and said foot end of said bed restraint having two horizontal side by side leg openings adjacent a lower distal end of said leg panel; there being affixed edgewardly to said top panel two downwardly vertically positioned lengthwise rectangular side panels adjacent said sides of said mat- tress and one downwardly vertically positioned front end panel adjacent said head end of said mattress; there being attached to a bottom lower edge of said front end panel and to lower bottom edges of said side panels adjacent said head end of said mattress a rectangular transverse horizontal end panel; there being two rectangular parallel horizontal bottom panels endwardly attached to said transverse horizontal end panel and lengthwise attached at outer edges thereof to said lower edges of said side panels with inner edges of said bottom panels interfacing centrally under said mattress; there being a long tie strap affixed to corners of said interfacing inner edges at said foot end of said parallel horizontal bottom panels for securing said restraint to framing members supporting said mattress.

2. The restraint device of claim 1 wherein said transverse bottom panel is attached to the ends of said parallel bottom panels with an elastic, stretchable seam.

* * * * *